United States Patent
Wellman et al.

(10) Patent No.: US 7,611,484 B2
(45) Date of Patent: Nov. 3, 2009

(54) METHODS AND DEVICES FOR TREATING DISEASED BLOOD VESSELS

(75) Inventors: Parris S. Wellman, Hillsborough, NJ (US); Kevin S. Weadock, Princeton, NJ (US)

(73) Assignee: Ethicon, Inc., Somerville, NJ (US)

( * ) Notice: Subject to any disclaimer, the term of this patent is extended or adjusted under 35 U.S.C. 154(b) by 977 days.

(21) Appl. No.: 10/833,614

(22) Filed: Apr. 28, 2004

(65) Prior Publication Data
US 2004/0204677 A1  Oct. 14, 2004

Related U.S. Application Data

(62) Division of application No. 09/965,949, filed on Sep. 28, 2001, now Pat. No. 6,808,518.

(51) Int. Cl.
*A61M 29/00* (2006.01)
(52) U.S. Cl. .............. 604/103.08; 604/96.01; 604/103.07; 606/159; 606/170; 606/192
(58) Field of Classification Search .......... 604/27, 604/48, 93, 96, 104, 105, 106, 107, 108, 604/109, 117, 158, 164.01, 164.09, 166, 604/170.01, 170.03, 192, 198, 272, 523, 604/103.07, 103.08; 606/159, 170, 192
See application file for complete search history.

(56) References Cited

U.S. PATENT DOCUMENTS

| 4,012,496 | A | 3/1977 | Schopflin et al. |
|---|---|---|---|
| 4,045,418 | A | 8/1977 | Sinclair |
| 4,057,537 | A | 11/1977 | Sinclair |
| 4,105,034 | A | 8/1978 | Shalaby et al. |
| 4,130,639 | A | 12/1978 | Shalaby et al. |
| 4,140,678 | A | 2/1979 | Shalaby et al. |
| 4,141,087 | A | 2/1979 | Shalaby et al. |
| 4,205,399 | A | 6/1980 | Shalaby et al. |
| 4,208,511 | A | 6/1980 | Shalaby et al. |
| 4,610,662 | A | 9/1986 | Weikl et al. |
| 4,636,195 | A | 1/1987 | Wolinsky |
| 5,087,244 | A | 2/1992 | Wolinsky et al. |
| 5,112,305 | A | 5/1992 | Barath et al. |
| 5,196,024 | A | 3/1993 | Barath |

(Continued)

OTHER PUBLICATIONS

Allcock. The Encyclopedia of Polymer Science. (1988) vol. 13 pp. 31-41. Wiley Intersciences, John Wiley & Sons.

(Continued)

*Primary Examiner*—Manuel A Mendez
(74) *Attorney, Agent, or Firm*—Nutter McClennen & Fish LLP

(57) ABSTRACT

The present invention provides a mechanism by which the physical properties of diseased blood vessel walls can be manipulated to achieve an effective vessel lumen diameter for a prolonged period of time. The methods and devices of the present invention selectively isolate and treat the medial or adventitial layers of these diseased blood vessels. The invention is based on the delivery of proteolytic enzymes and crosslinking agents via specialized delivery devices to a select layer of the diseased blood vessel wall. By isolating and treating these layers of the artery, collagen degrading and collagen crosslinking agents can be delivered so as to affect the diameter of the blood vessels and control blood flow therein.

3 Claims, 5 Drawing Sheets

U.S. PATENT DOCUMENTS

| | | | |
|---|---|---|---|
| 5,242,397 A | 9/1993 | Barath et al. | |
| 5,320,634 A | 6/1994 | Vigil et al. | |
| 5,328,470 A | 7/1994 | Nabel et al. | |
| 5,328,471 A | 7/1994 | Slepian | |
| 5,354,279 A | 10/1994 | Hofling | |
| 5,399,352 A | 3/1995 | Hanson | |
| 5,439,446 A | 8/1995 | Barry | |
| 5,464,395 A | 11/1995 | Faxon et al. | |
| 5,464,929 A | 11/1995 | Bezwada et al. | |
| 5,468,253 A | 11/1995 | Bezwada et al. | |
| 5,470,308 A * | 11/1995 | Edwards et al. | 604/22 |
| 5,538,504 A | 7/1996 | Linden et al. | |
| 5,595,751 A | 1/1997 | Bezwada et al. | |
| 5,597,579 A | 1/1997 | Bezwada et al. | |
| 5,599,307 A | 2/1997 | Bacher et al. | |
| 5,607,687 A | 3/1997 | Bezwada et al. | |
| 5,611,775 A | 3/1997 | Machold et al. | |
| 5,616,149 A | 4/1997 | Barath | |
| 5,618,552 A | 4/1997 | Bezwada et al. | |
| 5,620,698 A | 4/1997 | Bezwada et al. | |
| 5,645,850 A | 7/1997 | Bezwada et al. | |
| 5,648,088 A | 7/1997 | Bezwada et al. | |
| 5,681,281 A | 10/1997 | Vigil et al. | |
| 5,693,029 A | 12/1997 | Leonhardt | |
| 5,698,213 A | 12/1997 | Jamiolkowski et al. | |
| 5,700,583 A | 12/1997 | Jamiolkowski et al. | |
| 5,707,969 A | 1/1998 | Nabel et al. | |
| 5,713,863 A | 2/1998 | Vigil et al. | |
| 5,746,716 A | 5/1998 | Vigil et al. | |
| 5,762,600 A | 6/1998 | Bruchman et al. | |
| 5,776,182 A | 7/1998 | Bruchman et al. | |
| 5,807,306 A | 9/1998 | Shapland et al. | |
| 5,859,150 A | 1/1999 | Jamiolkowski et al. | |
| 5,873,852 A * | 2/1999 | Vigil et al. | 604/509 |
| 5,882,332 A | 3/1999 | Wijay | |
| 5,954,706 A | 9/1999 | Sahatjian | |
| 6,048,332 A | 4/2000 | Duffy et al. | |
| 6,077,257 A | 6/2000 | Edwards et al. | |
| 6,102,904 A | 8/2000 | Vigil et al. | |
| 6,152,141 A | 11/2000 | Stevens et al. | |
| 6,159,196 A | 12/2000 | Ruiz | |
| 6,197,013 B1 | 3/2001 | Reed et al. | |
| 6,210,392 B1 | 4/2001 | Vigil et al. | |
| 6,283,947 B1 | 9/2001 | Mirzaee | |
| 6,302,870 B1 * | 10/2001 | Jacobsen et al. | 604/272 |
| 6,309,370 B1 * | 10/2001 | Haim et al. | 604/66 |
| 6,398,757 B1 | 6/2002 | Varenne et al. | |
| 6,726,923 B2 | 4/2004 | Iyer et al. | |
| 2001/0020151 A1 | 9/2001 | Reed et al. | |

OTHER PUBLICATIONS

Cohn. Polymer Preprints (ACS Division of Polymer Chemistry) vol. 30(1), (1989) pp. 498.

Cohn and Younes. Journal of Biomaterials Research vol. 22 pp. 993-1009 (1988).

Heller Handbook of Biodegradable Polymers edited by Domb et al, Hardwood Academic Press, (1997) pp. 99-118.

Kemnitzer and Kohn 'Handbook of Biodegradable Polymers' edited by Domb et al Hardwood Academic Press (1997), pp. 251-272.

Vandorpe et al Handbook of Biodegradable Polymers edited by Domb et al Hardwood Academic Press (1997) pp. 161-182.

* cited by examiner

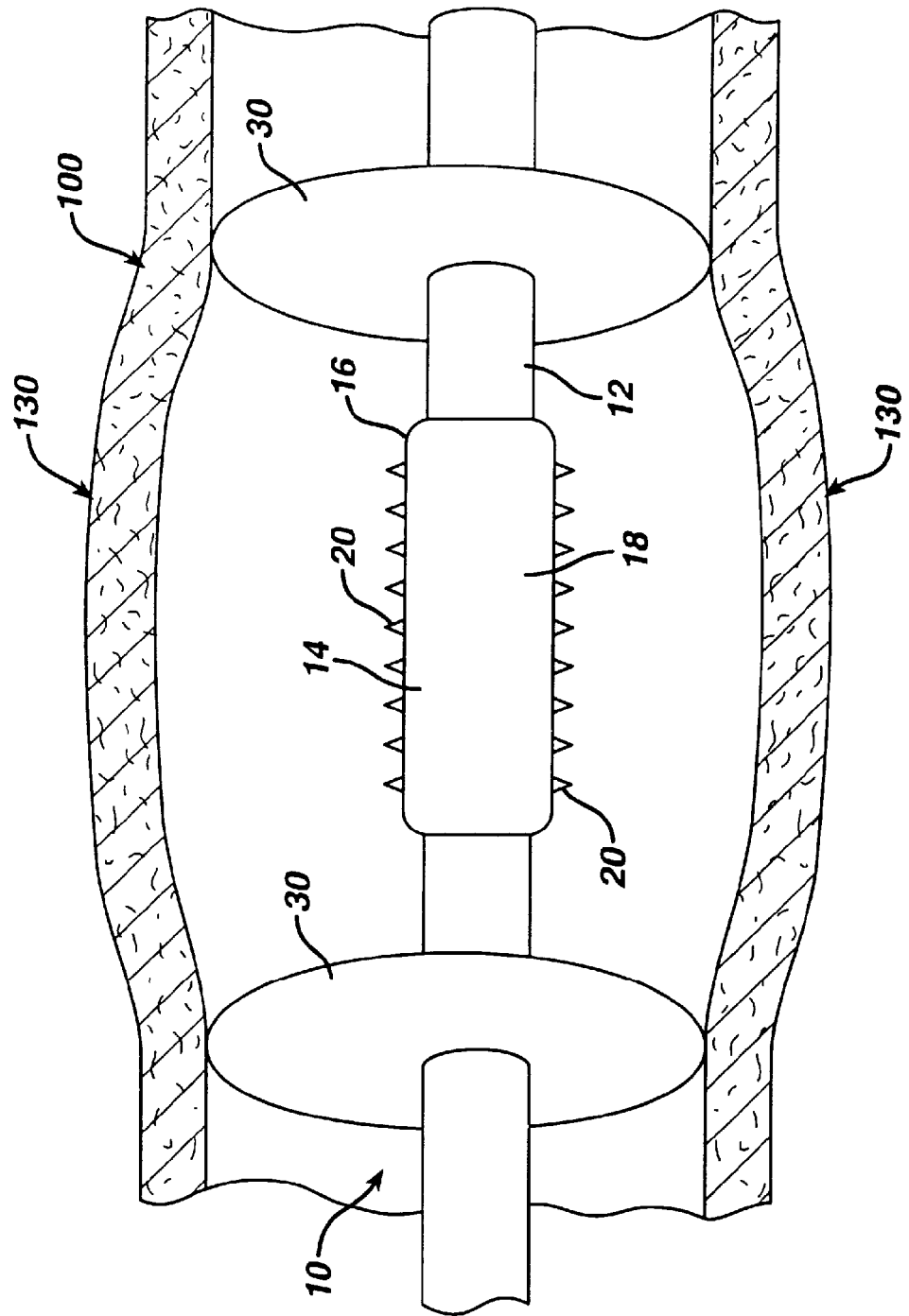

METHODS AND DEVICES FOR TREATING DISEASED BLOOD VESSELS

CROSS-REFERENCE TO RELATED APPLICATIONS

This application is a divisional of U.S. patent application Ser. No. 09/965,949, filed Sep. 28, 2001, entitled "Methods and Devices for Treating Diseased Blood Vessels."

FIELD OF THE INVENTION

The present invention relates generally to methods and devices for treating diseased blood vessels. More particularly, this invention relates to methods and devices for increasing the effective diameter of a diseased blood vessel and maintaining this effective diameter for a sufficient period of time.

BACKGROUND OF THE INVENTION

Current treatments for coronary artery disease include the use of stents, angioplasty, rotational atherectomy, cutting balloons, pharmaceutical agents, and lasers. All of these treatments attempt to increase blood flow at the narrowed region of the diseased vessel by compressing the intimal (innermost) aspect of the blood vessel against the medial (layer containing smooth muscle cells) and adventitial (outermost) layers of the vessel. These treatments often fail to increase the effective diameter of the coronary artery over a long period of time.

One of the drawback of interventional or catheter-based approaches is their inability to increase the coronary artery diameter for a prolonged period of time. Restenosis, a process that occurs when the smooth muscle cells and fibroblasts are stimulated to proliferate, frequently results after these interventional procedures. This re-narrowing of the blood vessel lumen reduces the effective diameter of the artery. With stents, their ability to correct diseased blood vessels can be hampered by their failure to traverse certain lesions, the difficulty in placing them in highly tortuous vessels, and the potential immunological problems associated with leaving the stents, which are foreign substances, in the vessel. When these treatments fail to adequately correct the situation, coronary artery bypass graft surgery (CABG) is usually required. However, this surgery is often expensive and results in prolonged incapacitation and post-surgical pain for the patient.

There is thus a need for a method and device for treating diseased blood vessels that avoids the aforementioned problems associated with stents, angioplasty, or CABG surgery. Particularly desirable are methods and devices that may enable a surgeon or interventional cardiologist to treat coronary artery disease by increasing the effective diameter of the coronary artery and maintaining this effective diameter for a sufficient period of time.

SUMMARY OF THE INVENTION

The present invention avoids the aforementioned problems associated with current treatments by providing a mechanism by which the physical properties of diseased blood vessel walls can be manipulated to achieve an effective vessel lumen diameter for a prolonged period of time. The methods and devices of the present invention selectively isolate and treat the medial or adventitial layers of these diseased blood vessels. These mechanisms involve disrupting the integrity of at least one of these layers to affect the physical properties, such as vessel wall stiffness, of the diseased region.

In an exemplary embodiment, a chemical treatment is utilized to disrupt the integrity of a blood vessel wall having an atherosclerotic plaque along its wall. The chemical treatment involves delivering a digestive agent to the adventitial layer of the blood vessel at the diseased region. The quantity of digestive agent should be sufficient to degrade the collagen of the blood vessel wall and preferably promote the growth of an aneurysm at the lesion. The digestive agent may comprise a proteolytic enzyme such as highly purified mammalian collagenase. The chemical treatment of the adventitial layer can occur either before or after an angioplasty to expand the diameter of the blood vessel at the plaque. The plaque can also be isolated from the remainder of the blood vessel prior to treatment.

In another embodiment, a mechanical treatment is utilized to disrupt the integrity of a blood vessel wall having an atherosclerotic plaque along its wall. The mechanical treatment involves puncturing the blood vessel wall at the diseased region to promote the growth of an aneurysm at the lesion. As with the chemical treatment, the mechanical disruption of the vessel wall can occur either before or after an angioplasty to expand the diameter of the blood vessel at the plaque. The plaque can also be isolated from the remainder of the blood vessel prior to treatment.

Additionally, with either the chemical or mechanical treatment, growth of the aneurysm may be controlled by delivering a crosslinking agent to a medial layer of the blood vessel wall at the diseased region. The quantity of crosslinking agent should be sufficient to promote crosslinking of the collagen of the blood vessel at the lesion. The crosslinking agent may be repeatedly delivered to the vessel wall until the collagen at the lesion site is sufficiently crosslinked. Preferably, the crosslinking agent comprises glutaraldehyde, formaldehyde, carbodiimides, or diisocyanates in physiologically buffered solutions.

In yet another embodiment of the invention, chemical treatment may be utilized to disrupt the integrity of a blood vessel wall having a naturally occurring aneurysm along its wall. In this instance, the chemical treatment involves delivering a crosslinking agent to the medial layer of the blood vessel wall at the diseased region. The quantity of crosslinking agent should be sufficient to promote crosslinking of the collagen of the blood vessel at the aneurysm. The crosslinking agent may be repeatedly delivered to the vessel wall until the collagen at the aneurysm is sufficiently crosslinked. Preferably, the crosslinking agent comprises glutaraldehyde, formaldehyde, carbodiimides, or diisocyanates in physiologically buffered solutions. The aneurysm may be isolated from the remainder of the blood vessel prior to treatment.

The biological agents employed in the methods of the present invention may be delivered with a catheter, a syringe, or by topical applicators such as with a film, coating, gel or sponge. The biological agents may also be directly injected into the blood vessel wall at the diseased region. For example, the blood vessel wall may be electroporated or sonoporated prior to injecting the agents into the wall. In addition, the vessel wall could be mechanically porated prior to treatment.

In one aspect of the invention, a catheter is provided for practicing the methods of the present invention. The catheter has an elongate body for insertion into a diseased blood vessel lumen. Mounted on the elongate body is an expandable balloon having an outer wall and an inflation lumen that is in fluid communication with a source of therapeutic agent. Extending from the outer wall of the balloon is at least one microneedle. The microneedle has an injection port extending from a base of the microneedle to a distal-most end for delivering the therapeutic agent to a select layer of the blood vessel wall.

The microneedle has a predetermined length sufficient to effectively puncture and extend into the select layer of the vessel wall to be treated when the balloon is fully expanded within the blood vessel lumen.

The microneedle may include a monitoring port that is in communication with a pressure sensor for detecting pressure changes between different layers of the vessel wall. The monitoring port enables the location of the distal-most end of the microneedle to be determined when it is within the blood vessel wall. The microneedle may also include a plurality of injection ports that are each capable of delivering a different therapeutic agent than the other injection ports within the microneedle. Preferably, the catheter has a plurality of microneedles arranged on the balloon and is capable of effecting delivery of the agent through a selected group of these microneedles to provide delivery in a predetermined spatial pattern.

In another aspect of the invention, the microneedle previously described can be provided on a syringe useful for practicing the methods of the present invention. The syringe can include an elongate body extending between a proximal end and a distal end. The syringe further includes a reservoir for holding the therapeutic agent. The microneedle can extend from the distal end of the elongate body. A deployment mechanism is included at the proximal end of the elongate body for effecting controlled injection of the therapeutic agent from the reservoir through the microneedle which is in fluid communication with the reservoir. The microneedle may preferably include a monitoring port that is in communication with a pressure sensor for detecting the difference in pressure inside the vessel wall and the pressure inside the vessel lumen. The monitoring port enables the location of the distal-most end of the microneedle to be determined when it is within the blood vessel wall.

In yet another aspect of this invention, a sponge is provided for practicing the methods of the present invention. The sponge has a body formed of biocompatible material loaded with a therapeutic agent for release at a later time. The therapeutic agent is effective for treating a select layer of the diseased blood vessel wall. The shape of the body may take the form of an annular ring so that the sponge can be thorascopically positioned circumferentially about the external surface of the blood vessel at the diseased region. The body may also include an adhesive layer extending about the outer surface to effect adhesion between the body and the blood vessel.

Further features of the invention, its nature and various advantages, will be more apparent from the accompanying drawings and the following detailed description of the drawings and the preferred embodiments.

BRIEF DESCRIPTION OF THE DRAWINGS

FIG. 3 is a cross-sectional view of the catheter of FIG. 1 partially deployed in a blood vessel having an aneurysm;

DETAILED DESCRIPTION OF THE DRAWINGS

Described herein are mechanisms for manipulating the physical properties of diseased blood vessels to achieve an effective vessel lumen diameter for a prolonged period of time. The methods and devices of the present invention selectively isolate and treat the medial or adventitial layers of these diseased blood vessels. Rather than attacking the lesion itself, the mode of treatment targets the blood vessel wall and involves disrupting the integrity of at least one of these layers to affect the physical properties, such as vessel wall stiffness, of the diseased region.

More specifically, the invention is based on the delivery of proteolytic enzymes and crosslinking agents via specialized delivery devices to a select layer of the diseased blood vessel wall. By isolating and treating these layers of the artery, collagen degrading and collagen crosslinking agents can be delivered so as to affect the diameter of the blood vessels and control blood flow therein. The present invention can be applied to both a blood vessel having an atherosclerotic plaque as well as a blood vessel having a naturally occurring aneurysm. Where a plaque is involved, the treatment focuses on the delivery of collagen degrading enzymes to the affected area of the vessel wall. Treatment of an aneurysm involves the delivery of collagen crosslinking agents to the vessel wall at the diseased area.

Figure 1:
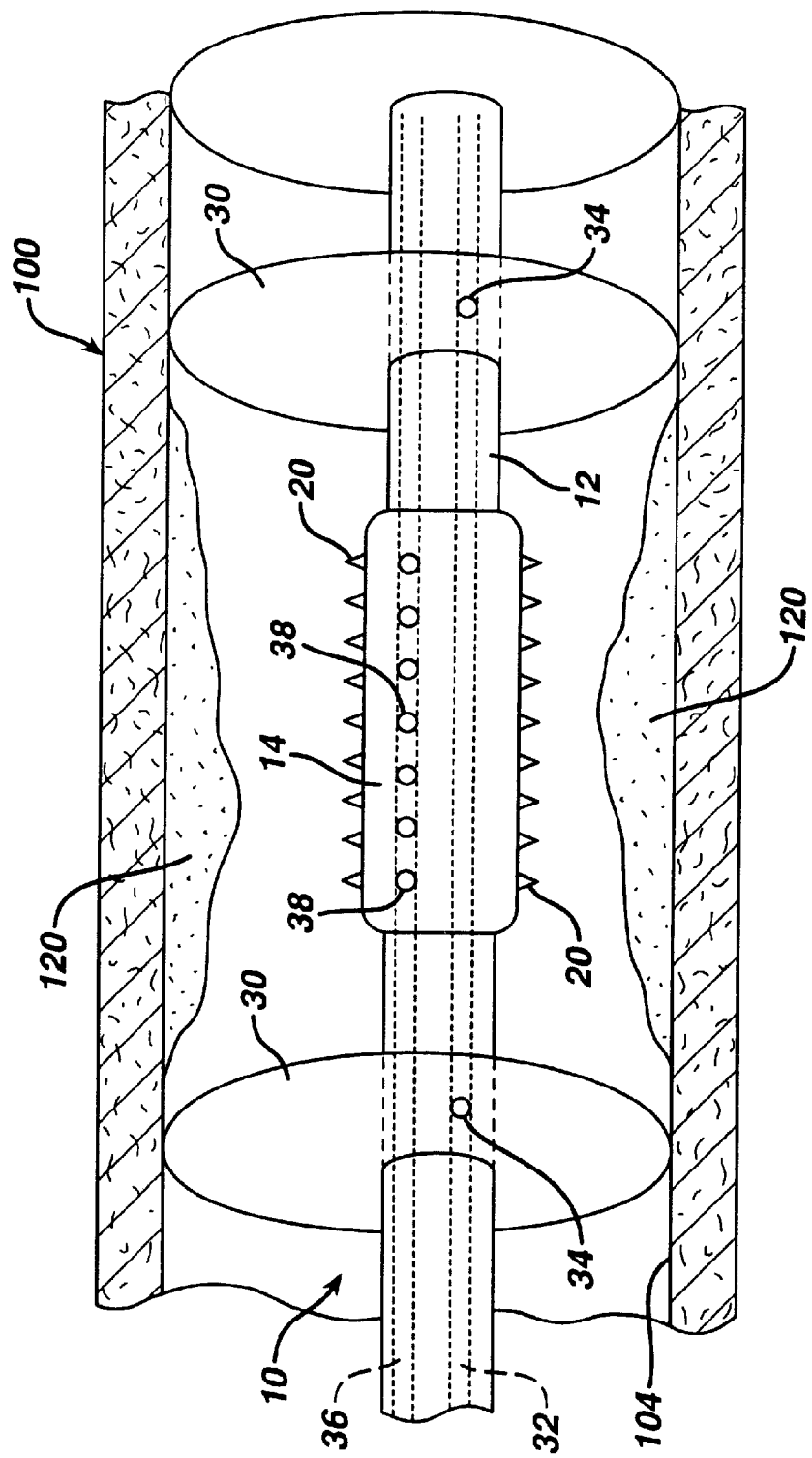
FIG. 1 is a cross-sectional view of a multi-balloon catheter of the present invention partially deployed in a blood vessel having an atherosclerotic plaque.

One such device for intravascularly delivering these enzymes and/or crosslinking agents is a specialized catheter 10 that is able to deliver a quantity of the enzyme and/or agent to a select layer of the diseased blood vessel wall 104. As illustrated in FIG. 1, catheter 10 has an elongate body 12 for insertion into a diseased blood vessel 100. Mounted on the elongate body 12 is an expandable balloon 14 having an outer wall 16 and an inflation lumen 18 that is in fluid communication with a source of enzyme and/or agent. Balloon 14 can be dimensioned as a typical angioplasty balloon. Extending from the outer wall 16 of the balloon 14 are a plurality of microneedles 20 to enable the fluid to be selectively injected into a component of the vessel wall 104.

Figure 2A:
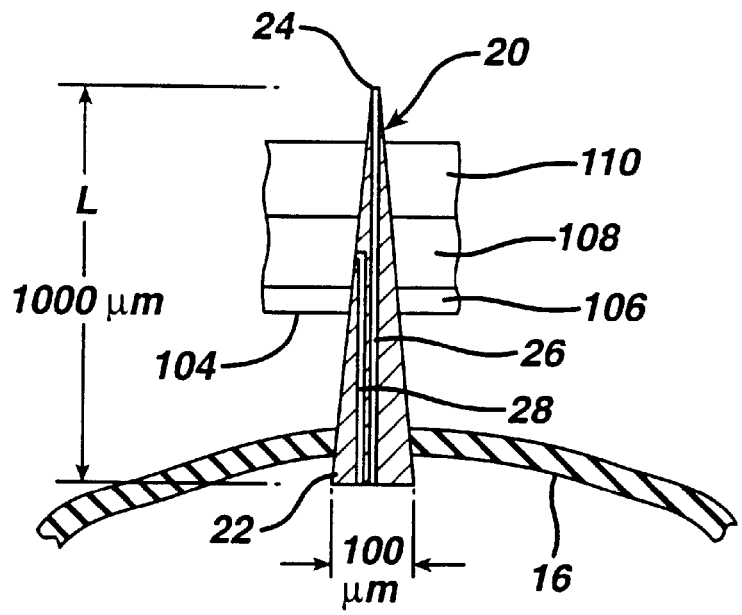
FIG. 2A is a partial cut-away view of a microneedle of the catheter of FIG. 1.

When balloon 14 is expanded, microneedles 20 project through the intima (inner layer) 106 and into the media (middle layer) 108 and adventitia (outer layer) 110, as shown in FIG. 2A. Each of the microneedles 20 has a delivery lumen, or injection port 26 extending from a base 22 of the microneedle 20 to a distal-most end 24 for delivering the enzyme and/or agent to a select layer (intimal 106, medial 108, or adventitial 110) of the blood vessel wall 104. The microneedle 20 has a predetermined length L sufficient to effectively puncture and extend into the select layer of the vessel wall 104 to be treated when the balloon 14 is fully expanded within the blood vessel lumen 102. The length L of microneedle 20 can be chosen after the vessel 100 has been imaged and the extent of the disease is assessed. For instance, the physician may wish to treat the medial layer 108 to prevent intimal hyperplasia. This might require a different needle length L than that required for increasing the effective diameter of the vessel 100 by deliberate injection of collagenase into the tunica adventitia 110.

As shown in FIG. 2A, each microneedle 20 can include a monitoring port or lumen 28 that is in communication with a pressure sensor (not shown) for detecting the difference in pressure inside the vessel wall 104 and the pressure inside the lumen 102. The monitoring port 28 enables the location of the distal-most end 24 of the microneedle 20 to be determined when it is within the blood vessel wall 102. For example, if the adventitia 108 of the vessel 100 were perforated and the distal-most end, or tip 24 passed out into the space surrounding the vessel 100, the pressure change could be sensed, and the position of the tip 24 of the microneedle 20 would be known.

Figure 2B:
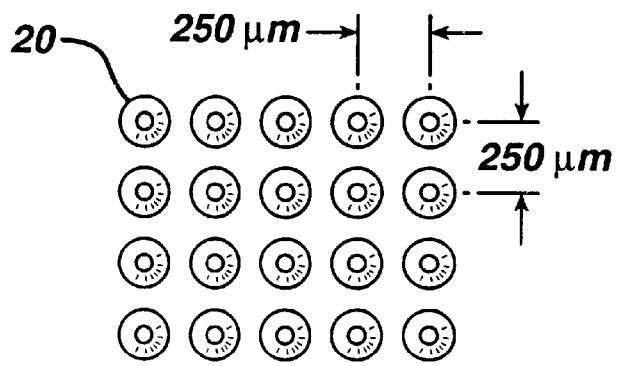
FIG. 2B is a top-down view of an array of microneedles.

It is contemplated that the microneedle 20 can include multiple injection ports 26 that are each capable of delivering a different therapeutic agent than the other injection ports within the microneedle 20. Though catheter 10 can include a single microneedle 10, preferably catheter 10 has a plurality of microneedles 20 arranged on the balloon 14 in a predefined pattern as shown in FIG. 1. By modifying the spacing of the microneedles 20, or by selectively loading the microneedles 20 in a densely packed array such that each microneedle 20 is about 250 microns apart from one another as shown in FIG. 2B, it is possible to change the dosage and spatial delivery pattern of the active agent by effecting delivery in only a selection of these microneedles 20.

In the exemplary embodiment illustrated in FIG. 2A, microneedle 20 has a base 22 in the range of about 100 microns wide and a length L in the range of about 1000 microns. Microneedles 20 can be fabricated by micro-machining, or electrodeposition on a micromachined master and be coupled to the balloon surface by overmolding them with the balloon 14. This would provide a seal between the balloon and the needle. The microneedle length and density of the array would vary according to the layer of the vessel to be treated but would be on the order of 1 mm for treating diseased coronary arteries. One of ordinary skill in the art will readily appreciate that the dimensions of the microneedles 20 can be altered to meet the requirements of a desired application.

Where it is desirable to isolate the diseased region of the blood vessel 100 from the healthy remainder of the vessel 100 prior to treatment, end balloons 30 can be deployed. As shown in FIGS. 1 and 3, catheter 10 may also include a pair of end balloons 30 situated on either side of balloon 14. When fully expanded, end balloons 30 enable the diseased region of the blood vessel 100 to be isolated from blood flow therethrough. This multi-balloon catheter 10 may be useful in isolating a lesion and administering one or more fibrinolytic substances, collagenase, chelating agents, and crosslinking agents. However, the extent of disease may preclude the use of the multi-balloon catheter 10 since diffusion of the agent through the lesion may be impaired or difficult to control. In order to allow blood to flow through the lesion while treatment is occurring, a central lumen (not shown) that shunts the blood from one side of the lesion to the other can be included.

FIG. 1 illustrates the multi-balloon catheter 10 partially deployed in a diseased blood vessel 100 having an atherosclerotic plaque 120 along its wall 104. Extending through catheter 10 is a channel 32 in communication with a saline source for carrying the saline through ports 34 to fill end balloons 30. As shown, end balloons 30 are fully expanded to block the plaque 120 from the remainder of the blood vessel 100. To effect chemical treatment of the diseased region, a digestive agent is pumped through channel 36 within elongate body 12 and out ports 38 to fill balloon 14. As balloon 14 is expanded, microneedles 20 puncture through the vessel wall 104 so that the distal-most end 24 reaches the adventitial (outermost) layer 110 of the vessel wall 104. The digestive agent contained within balloon 14 can then be injected into the adventitial layer 110 of the blood vessel 100 at the diseased region. The quantity of digestive agent should be sufficient to degrade the collagen of the blood vessel wall 104 and preferably promote the growth of an aneurysm at the lesion, the extent of which can be controlled by the amount of digestive agent to be delivered. The digestive agent may comprise a proteolytic enzyme such as highly purified mammalian collagenase. Up to 250 ml of 20,000 U/ml collagenase can be used. Bacterial collagenase can also be used as well. Though FIG. 1 shows a narrowing of the vessel 100 at plaque 120, such chemical treatment of the adventitial layer 110 can occur either before or after an angioplasty to expand the diameter of the blood vessel 100 at the plaque 120.

Figure 4A:
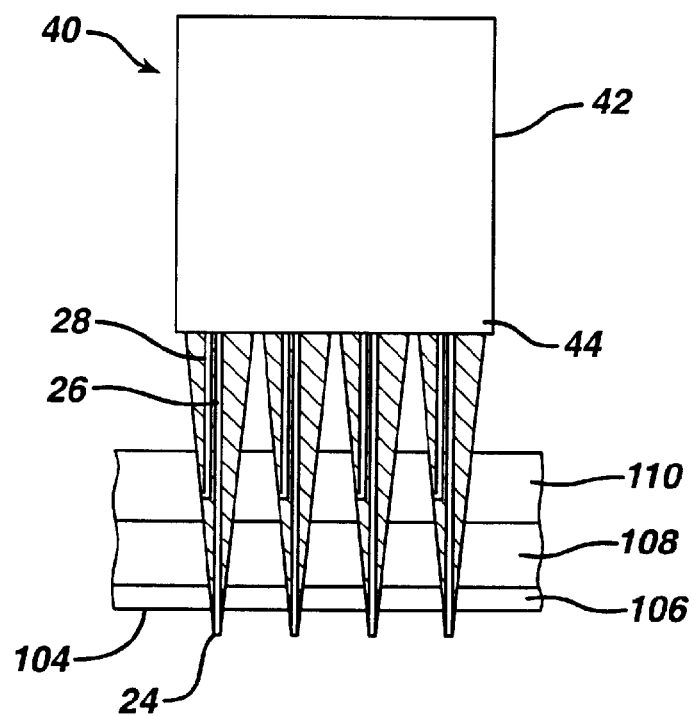
FIG. 4A is a partial cut-away view of a syringe of the present invention.
Figure 4B:
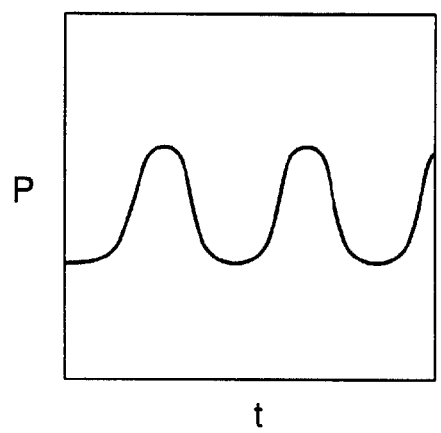
FIG. 4B is a graph of an exemplary arterial pressure waveform.

It is possible to affect the physical properties of the vessel wall 104 without chemicals. Catheter 10 enables not only chemical but mechanical disruption of the integrity of the blood vessel wall 104. For instance, microneedles 20 can be used solely to puncture the blood vessel wall 104 at the diseased region rather than to deliver any therapeutic agent (s). Once the vessel wall 104 has been disrupted by producing at least one puncture in the blood vessel wall, and blood flow is allowed to pass through the diseased region, an aneurysm can result at the lesion. Proper placement of the microneedles 20 is ensured by penetrating the vessel 100 until an arterial pressure waveform such as the one shown in FIG. 4B is generated through the monitoring lumen and visually displayed on an attached monitor. It is envisioned that the holes left in the vessel wall 104 will be less than 50 microns in diameter, which should not pose a risk of vessel leakage. As with the chemical treatment, the mechanical disruption of the vessel wall 104 can occur either before or after an angioplasty to expand the diameter of the blood vessel 100 at the plaque 120. The plaque 120 can also be isolated from the remainder of the blood vessel 100 prior to treatment.

Additionally, with either the chemical or mechanical treatment, growth of the aneurysm may be controlled by delivering a crosslinking agent to a medial layer 108 of the blood vessel wall 104 at the diseased region. The quantity of crosslinking agent should be sufficient to promote crosslinking of the collagen of the blood vessel at the lesion. The crosslinking agent may be repeatedly delivered to the vessel wall until the collagen at the lesion site is sufficiently crosslinked. Preferably, the crosslinking agent comprises glutaraldehyde, formaldehyde, carbodiimides, or diisocyanates in physiologically buffered solutions. In the most preferred embodiment, a solution of 0.37% (weight/volume) of formaldehyde in phosphate buffered saline is used.

Other agents such as conjugated monoclonal antibodies and paralyzing agents can also be delivered to the medial layer 108 so as to regulate smooth muscle cell activity during treatment. For instance, agents such as extracts of clostridia tetani, auger emitters, or monoclonal antibodies conjugated to radioisotopes or cell specific toxins can be used to supplement the treatment and control the muscle cells of the vessel wall 104 while the collagen is being degraded or crosslinked.

The catheter 10 of the present invention can also be used to chemically treat a blood vessel 100 having a naturally occurring aneurysm 130 along its wall 104, as shown in FIG. 3. In this instance, the chemical treatment involves expanding balloon 14 so that microneedles 20 extend into the medial layer 108 of the vessel wall 108 at the diseased region and delivering thereto a collagen crosslinking agent. The quantity of crosslinking agent should be sufficient to promote crosslinking of the collagen of the blood vessel 100 at the aneurysm 130. The crosslinking agent may be repeatedly delivered to the vessel wall 104 until the collagen at the aneurysm is sufficiently crosslinked. Preferably, the crosslinking agent comprises glutaraldehyde, formaldehyde, carbodiimides, or diisocyanates in physiologically buffered solutions. As illustrated in FIG. 3, the aneurysm 130 may be isolated from the remainder of the blood vessel 100 prior to treatment by the use of end balloons 30.

Additionally, it is contemplated that the collagen degrading agent and the collagen crosslinking agent may also be directly injected into the blood vessel wall at the diseased region. For example, the blood vessel wall may be electroporated or sonoporated to create openings within the blood vessel wall and allow the introduction of the active agents. Thereafter, the agents may be injected into the wall using a catheter having high pressure injection ports (not shown) without the need for microneedles.

Another device that enables the direct injection of agents into the blood vessel wall is a specialized syringe 40 having microneedles 20 similar to the ones on the balloon surface 16 of catheter 10. As shown in FIG. 4A, the syringe 40 can include an elongate body 42 extending between a proximal end (not shown) and a distal end 44. The syringe 40 further includes a reservoir (not shown) for holding the therapeutic agent and microneedles 20 extending from the distal end 44 that selectively deliver the agent to the desired layer of the blood vessel. A deployment mechanism (not shown) is included at the proximal end of the elongate body 42 for effecting controlled injection of the therapeutic agent from the reservoir through the microneedles 20 which are in fluid communication with the reservoir. It is contemplated that any conventional deployment mechanism applicable to syringes can be utilized. The microneedles 20 may preferably include a monitoring port 28 that is in communication with a pressure sensor for detecting pressure changes as graphed between different layers of the vessel wall 104. The monitoring port 28 enables the location of the distal-most end 24 of the microneedle 20 to be determined when it is within the blood vessel wall 104. Additionally, syringe 40 may also include a flange (not shown) to control the depth at which the microneedles 20 extend into the patient.

Syringe 40 can be used in thoracoscopic delivery of the agent(s). The syringe 40 can be introduced into a trocar placed between a patient's ribs. With the aid of a visualization tool such as an endoscope, the distal end 24 of the syringe 40 can be directed to the surface of the patient's heart, and more particularly to the surface of a coronary artery. By injecting an enzyme like collagenase in a controlled manner, the surgeon can deliberately increase the diameter of the artery. The procedure can then be repeated some time later, if necessary, to quench the enzymatic reaction or deliver a crosslinking agent to fix the arterial diameter. Extravascular delivery directly to the adventitial layer avoids the potential of collagenase or crosslinking agent from affecting healthy tissue. Proper placement of the microneedles 20 can be ensured by penetrating the vessel 100 until an arterial pressure waveform like that shown in FIG. 4B is generated through the monitoring lumen 28 and visually displayed on an attached monitor.

Figure 5:
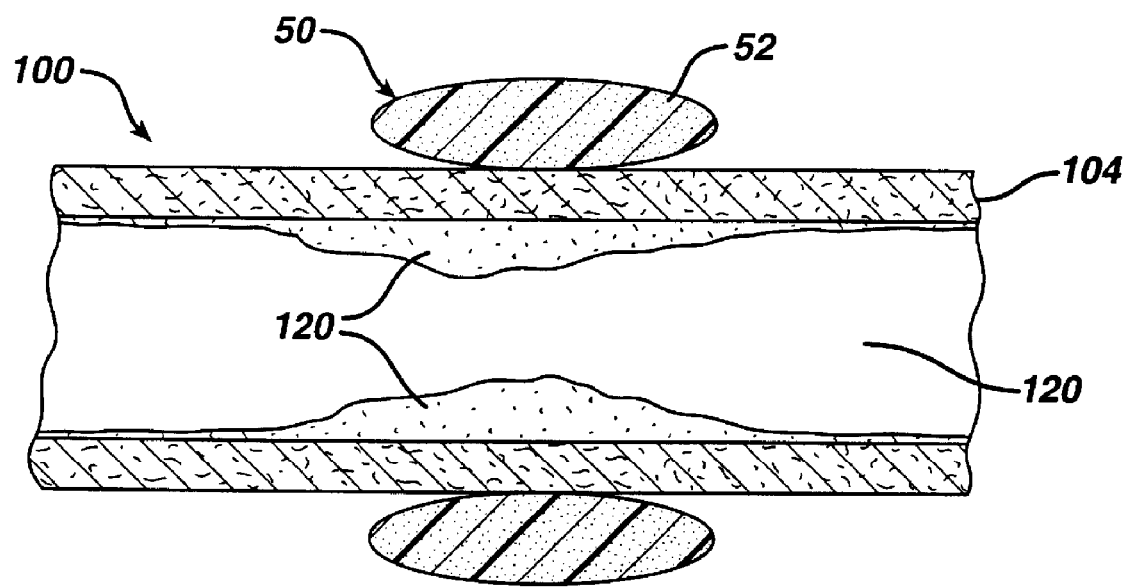
FIG. 5 is a cross-sectional view of a sponge of the present invention deployed on a blood vessel with a partial occlusion.

Topical drug applicators such as films, coatings, gels, or sponges can also be used with the present invention. For example, another device provided is a sponge 50 loaded with an active agent to be placed on the affected vessel 100. The sponge 50, shown in FIG. 5, has a body 52 formed of biocompatible material loaded with a therapeutic agent(s) for release at a later time. The therapeutic agent is effective for treating a select layer of the diseased blood vessel wall 104. As illustrated, the shape of the body may take the form of an annular ring so that the sponge 50 can be thoracoscopically positioned circumferentially about the external surface of the blood vessel 100 at the diseased region. The vessel 100 may be dissected away from the surrounding tissue and the sponge 50 passed under the vessel 100 and placed onto the vessel wall 104 at the appropriate position to provide not only delayed drug delivery but also a mechanical support for treating the diseased region of the blood vessel 100. The body 52 may also include an adhesive layer extending about the outer surface to effect adhesion between the body 52 and the blood vessel 100.

It is contemplated that sponge 50 can also be composed of a suitable bioabsorbable polymer or copolymer. Exemplary materials include polylactic acid-polyglycolic acid (PLA-PGA), with a predominant fraction of PGA. Other bioabsorbable polymers can be used to make the scaffold according to the present invention. Examples of suitable biocompatible, bioabsorbable polymers include polymers selected from the group consisting of aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) and blends thereof. For the purpose of this invention aliphatic polyesters include, but are not limited to, homopolymers and copolymers of lactide (which includes lactic acid, D-, L- and meso lactide), glycolide (including glycolic acid), $\epsilon$-caprolactone, p-dioxanone (1,4-dioxan-2-one), trimethylene carbonate (1,3-dioxan-2-one), alkyl derivatives of trimethylene carbonate, $\gamma$-valerolactone, $\beta$-butyrolactone, $\gamma$-butyrolactone, $\epsilon$-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan -2-one 2,5-diketomorpholine, pivalolactone, $\alpha$, $\alpha$-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. Poly(iminocarbonates), for the purpose of this invention, are understood to include those polymers as described by Kemnitzer and Kohn, in the *Handbook of Biodegradable Polymers*, edited by Domb, et. al., Hardwood Academic Press, pp. 251-272 (1997). Copoly (ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g. PEO/PLA). Polyalkylene oxalates, for the purpose of this invention, include those described in U.S. Pat. Nos. 4,208,511; 4,141,087; 4,130,639; 4,140,678; 4,105,034; and 4,205,399. Polyphosphazenes, co-, ter- and higher order mixed monomer based polymers made from L-lactide, D,L-lactide, lactic acid, glycolide, glycolic acid, para-dioxanone, trimethylene carbonate and $\epsilon$-caprolactone such as are described by Allcock in *The Encyclopedia of Polymer Science*, Vol. 13, pages 31-41, Wiley Intersciences, John Wiley & Sons, 1988 and by Vandorpe, et al in the *Handbook of Biodegradable Polymers*, edited by Domb, et al, Hardwood Academic Press, pp. 161-182 (1997). Polyanhydrides include those derived from diacids of the form HOOC-$C_6H_4$—O—$(CH_2)_m$—O—$C_6H_4$—COOH, where m is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in *Handbook of Biodegradable Polymers*, edited by Domb, et al, Hardwood Academic Press, pp. 99-118 (1997).

Exemplary bioabsorbable, biocompatible elastomers include but are not limited to elastomeric copolymers of $\epsilon$-caprolactone and glycolide (including polyglycolic acid) with a mole ratio of $\epsilon$-caprolactone to glycolide of from about 35:65 to about 65:35, more preferably from 45:55 to 35:65;

elastomeric copolymers of ε-caprolactone and lactide (including L-lactide, D-lactide, blends thereof, and lactic acid polymers and copolymers) where the mole ratio of ε-caprolactone to lactide is from about 35:65 to about 65:35 and more preferably from 45:55 to 30:70 or from about 95:5 to about 85:15; elastomeric copolymers of p-dioxanone (1,4-dioxan-2-one) and lactide (including L-lactide, D-lactide, blends thereof, and lactic acid polymers and copolymers) where the mole ratio of p-dioxanone to lactide is from about 40:60 to about 60:40; elastomeric copolymers of ε-caprolactone and p-dioxanone where the mole ratio of ε-caprolactone to p-dioxanone is from about from 30:70 to about 70:30; elastomeric copolymers of p-dioxanone and trimethylene carbonate where the mole ratio of p-dioxanone to trimethylene carbonate is from about 30:70 to about 70:30; elastomeric copolymers of trimethylene carbonate and glycolide (including polyglycolic acid) where the mole ratio of trimethylene carbonate to glycolide is from about 30:70 to about 70:30; elastomeric copolymers of trimethylene carbonate and lactide (including L-lactide, D-lactide, blends thereof, and lactic acid polymers and copolymers) where the mole ratio of trimethylene carbonate to lactide is from about 30:70 to about 70:30; and blends thereof. Examples of suitable bioabsorbable elastomers are described in U.S. Pat. Nos. 4,045,418; 4,057,537 and 5,468,253.

While the present invention has been described and illustrated in relation to cardiac blood vessels such as coronary arteries, the methods and devices described herein are equally suitable for use in vessels of the brain, stomach, and other parts of the body. The present invention is especially appropriate for treating naturally occurring aneurysms within the brain and stomach, as well as coronary arteries having atherosclerotic plaques. Further, modifications to the volume and concentration of the collagen degrading and crosslinking agents, as well as the frequency of delivery of the agents, can be made to the methods herein described as appropriately determined by the surgeon.

It will be understood that the foregoing is only illustrative of the principles of the invention, and that various modifications can be made by those skilled in the art without departing from the scope and spirit of the invention. All references cited herein are expressly incorporated by reference in their entirety.

What is claimesd is:

1. A catheter for delivering a therapeutic agent to a blood vessel having a diseased region along a vessel wall thereof, comprising:
    an elongate body adapted to be inserted into a blood vessel lumen;
    at least one expandable balloon mounted on the elongate body, the expandable balloon having an outer wall and an inflation lumen in fluid communication with a source of therapeutic agent; and
    at least one microneedle extending from the outer wall of the at least one balloon, the at least one microneedle having at least one injection port extending from a base of the microneedle to a distal-most end for delivering the therapeutic agent to a select layer within the vessel wall;
    wherein when the balloon is fully expanded within the blood vessel lumen at the diseased region, the microneedle effectively punctures and extends into the select layer of the vessel wall to be treated.

2. The catheter of claim 1, wherein the at least one microneedle includes a monitoring port for determining the location of the distal-most end of the microneedle within the blood vessel wall, the microneedle being in communication with a pressure sensor for detecting the difference in pressure inside the vessel wall and the pressure inside the vessel lumen.

3. The catheter of claim 1, wherein the catheter has a plurality of microneedles, and the catheter is capable of injecting the therapeutic agent trough a selected group of the plurality of microneedles to provide delivery in a predetermined spatial pattern.

* * * * *

UNITED STATES PATENT AND TRADEMARK OFFICE
CERTIFICATE OF CORRECTION

PATENT NO. : 7,611,484 B2
APPLICATION NO. : 10/833614
DATED : November 3, 2009
INVENTOR(S) : Wellman et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1374 days.

Signed and Sealed this

Twelfth Day of October, 2010

David J. Kappos
*Director of the United States Patent and Trademark Office*